(12) United States Patent
Kim et al.

(10) Patent No.: US 11,333,658 B2
(45) Date of Patent: May 17, 2022

(54) URINE TEST STRIP COMPRISING TIMER, AND METHOD FOR DETECTING AND ANALYZING URINE TEST STRIP

(71) Applicant: INDUSTRY-UNIVERSITY COOPERATION FOUNDATION HANYANG UNIVERSITY, Seoul (KR)

(72) Inventors: Whoi-Yul Kim, Seoul (KR); Jong Woo Lim, Seoul (KR); Min Su Kim, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 1 day.

(21) Appl. No.: 16/481,594

(22) PCT Filed: Jan. 2, 2018

(86) PCT No.: PCT/KR2018/000005
§ 371 (c)(1),
(2) Date: Jul. 29, 2019

(87) PCT Pub. No.: WO2019/107666
PCT Pub. Date: Jun. 6, 2019

(65) Prior Publication Data
US 2020/0249220 A1 Aug. 6, 2020

(30) Foreign Application Priority Data
Nov. 29, 2017 (KR) .................. 10-2017-0161305

(51) Int. Cl.
*G01N 33/493* (2006.01)
*G01N 21/78* (2006.01)

(52) U.S. Cl.
CPC ........... *G01N 33/493* (2013.01); *G01N 21/78* (2013.01)

(58) Field of Classification Search
CPC ...... G01N 33/493; G01N 21/78; A61B 10/00; A61B 10/007
See application file for complete search history.

(56) References Cited

U.S. PATENT DOCUMENTS

2012/0189509 A1* 7/2012 Hsiao ................. G01N 21/8483
422/400
2013/0034908 A1 2/2013 Barstis et al.
(Continued)

FOREIGN PATENT DOCUMENTS

CN 105899935 A 8/2016
JP 09-101305 A 4/1997
(Continued)

OTHER PUBLICATIONS

International Search Report issued from PCT International Application No. PCT/KR2018/000005 dated Aug. 23, 2018.

*Primary Examiner* — Jennifer Wecker
*Assistant Examiner* — Oyeleye Alexander Alabi (57) ABSTRACT

A method of detecting a urine test strip from a photographed image of the urine test strip is disclosed. The disclosed method of detecting a urine test strip includes: receiving input of a urine test strip image, which is a photographed image of a urine test strip including a first and a second marker; detecting a first and a second marker image within the urine test strip image; detecting an area between the first and second marker images within the urine test strip image; and detecting a reagent pad and a colorimetric table in the urine test strip image by matching an area of interest, which represents a position of the reagent pad and the colorimetric (Continued)

table in the urine test strip image, with the area between the first and second marker images.

8 Claims, 4 Drawing Sheets

(56) References Cited

U.S. PATENT DOCUMENTS

| | | |
|---|---|---|
| 2015/0160245 A1 | 6/2015 | Lieberman et al. |
| 2015/0286803 A1* | 10/2015 | Myers .................... G16H 10/40 235/375 |
| 2016/0370389 A1 | 12/2016 | Barstis et al. |

FOREIGN PATENT DOCUMENTS

| | | |
|---|---|---|
| JP | 09101305 A | 4/1997 |
| KR | 10-2014-0130879 A | 11/2014 |
| KR | 10-2015-0115971 A | 10/2015 |
| KR | 10-2016-0111693 A | 9/2016 |
| KR | 10-1656712 B1 | 9/2016 |
| WO | 2013149598 A1 | 10/2013 |

* cited by examiner

URINE TEST STRIP COMPRISING TIMER, AND METHOD FOR DETECTING AND ANALYZING URINE TEST STRIP

CROSS-REFERENCE TO RELATED APPLICATIONS

This application is a National Stage Entry of PCT International Application No. PCT/KR2018/000005, which was filed on Jan. 2, 2018, and which claims priority under 35 U.S.C 119(a) to Korean Patent Application No. 10-2017-0161305 filed with the Korean Intellectual Property Office on Nov. 29, 2017. The disclosures of the above patent applications are incorporated herein by reference in their entirety.

BACKGROUND

1. Technical Field

The present disclosure relates to a urine test strip including a timer and a method of detection and a method of analysis for a urine test strip. More particularly, the present disclosure relates to a urine test strip that includes a timer to notify the user of the time point for photographing the urine test strip for a urine test, as well as to methods of detecting and analyzing the urine test strip from a photographed image of the urine test strip.

2. Description of the Related Art

There are ongoing advances in methods of measuring biometric information through specimens collected from the body. While urine or blood samples are generally used as specimens, advances in measurement methods have led to the development of methods that measure biometric information, such as information related to diabetes, etc., by using sweat or tear samples as specimens. There are also developments under way of methods for measuring biometric information by collecting specimens from saliva, exhalation, etc.

As a typical method of measuring biometric information using a sample, it is possible to measure biometric information in a simple manner through a qualitative analysis involving visually checking the reactive result of urine on a urine test strip to determine whether the result is positive or negative. As regards measuring biometric information, numerous reagents are being required for various diseases, and there is also a demand for qualitative evaluations, i.e. determining the extent of a condition based on a measurement figure, in addition to the qualitative analysis of testing for a positive/negative result.

Although it has become possible to acquire various information, such as blood sugar levels, acidity (pH), protein levels, etc., there is the problem of having to provide measurement equipment individually according to the types of information measured. Moreover, as the measurement equipment is large in size and relatively expensive, and since the measurement methods require expert knowledge, access to such methods was limited only to certain professionals such as doctors, clinical technologists, etc.

To resolve this problem, there is a surge in efforts for developing household, portable measurement devices that can be easily used by regular persons, and in recent times, there have been research efforts focusing on methods of measuring biometric information by inputting specimen information into a mobile terminal such as a smart phone. Current development efforts concerning techniques that utilize optical image sensors, such as a camera included on a device, to analyze a strip having a urine sample are gaining much attention, and for the purpose of accurately analyzing the reaction between urine and the reagent pad attached to the strip, research is actively under way on methods of analyzing the degree of color change of the reagent pad and applying corrections to obtain an accurate value for the degree of color change.

In addition, for an accurate analysis of reactions undergone by the urine, there has also been developed a strip that includes a colorimetric table arranged around the reagent pad.

SUMMARY OF THE INVENTION

An aspect of the present disclosure is to provide a method of detecting a urine test strip from a photographed image of the urine test strip for the purpose of performing an image-based color analysis of the reagent pad reacted with urine.

Another aspect of the present disclosure is to provide a urine test strip that uses a timer to provide the user with information regarding the time point at which the urine test strip should be photographed after the time of urine immersion.

Also, another aspect of the present disclosure is to provide a method of analyzing a urine test strip where an image of a urine test strip including a timer that shows the time of urine immersion is analyzed to provide information as regards whether or not the time point of photographing an image to analyze the degree of color change of the reagent pad is appropriate.

To achieve the objectives above, an embodiment of the present disclosure provides a method of detecting a urine test strip that includes: receiving input of a urine test strip image, which is a photographed image of a urine test strip including a first and a second marker; detecting a first and a second marker image within the urine test strip image; detecting an area between the first and second marker images within the urine test strip image; and detecting a reagent pad and a colorimetric table in the urine test strip image by matching an area of interest, which represents a position of the reagent pad and the colorimetric table in the urine test strip image, with the area between the first and second marker images.

Also, another embodiment of the present disclosure for achieving the objectives above provides a method of analyzing a urine test strip that includes: acquiring a urine test strip image by photographing a urine test strip, where the urine test strip includes a timer configured to indicate a urine immersion time; determining whether or not a photography time lies within a color analysis time range by analyzing a timer image included in the urine test strip image, where the color analysis time range is defined by a preset duration of time after the urine immersion time; and displaying information based on the result of the determining.

Also, yet another embodiment of the present disclosure for achieving the objectives above provides a urine test strip having a timer that includes: a multiple number of reagent pads; a colorimetric table arranged in a surrounding of each of the reagent pads; a timer that is configured to indicate a urine immersion time and includes an immersion area for immersion in urine; and a waterproof film configured to prevent urine immersion for remaining areas of the timer other than the immersion area.

An embodiment of the present disclosure makes it possible to accurately detect the area where the reagent pads and colorimetric tables are located in a urine test strip image by using the actual sizes of markers and the urine test strip.

Also, an embodiment of the present disclosure can use a timer to indicate the accurate analysis time for the urine test strip.

DETAILED DESCRIPTION OF THE INVENTION

As the invention allows for various changes and numerous embodiments, particular embodiments will be illustrated in the drawings and described in detail in the written description. However, this is not intended to limit the present disclosure to particular modes of practice, and it is to be appreciated that all changes, equivalents, and substitutes that do not depart from the spirit and technical scope of the present disclosure are encompassed in the present disclosure. In describing the drawings, similar reference numerals are used for similar elements.

The present disclosure can be used for an image-based analysis of the degree of color change of a reagent pad on a urine test strip, and an aspect of the present disclosure is to propose a method of accurately detecting the urine test strip from a photographed urine test strip image taken of the urine test strip.

In recent times, there has been developed a urine test strip on which a colorimetric table is arranged together around the reagent pad so as to allow the user to readily check the degree of color change of the reagent pad, but as it is not always easy for a person to check the degree of color change by visual inspection only, there is also being developed an algorithm using image processing technology for checking the degree of color change more accurately compared to the case of visual inspection based on the unassisted eye.

In order to identify the degree of color change of reagent pads from a urine test strip image, it is necessary to first accurately detect the reagent pads and colorimetric tables on the urine test strip, and as such, an aspect of the present disclosure proposes a method of accurately detecting the reagent pads and colorimetric tables of the urine test strip within the urine test strip image to read the color values of the reagent pads and colorimetric tables.

Methods based on the present disclosure can be applied in detecting not only to urine test strips but also other strips for testing various specimens, such as blood, sweat, saliva, etc., in a manner similar to urine testing.

Certain embodiments of the present disclosure are described below in further detail with reference to the accompanying drawings.

Figure 1:
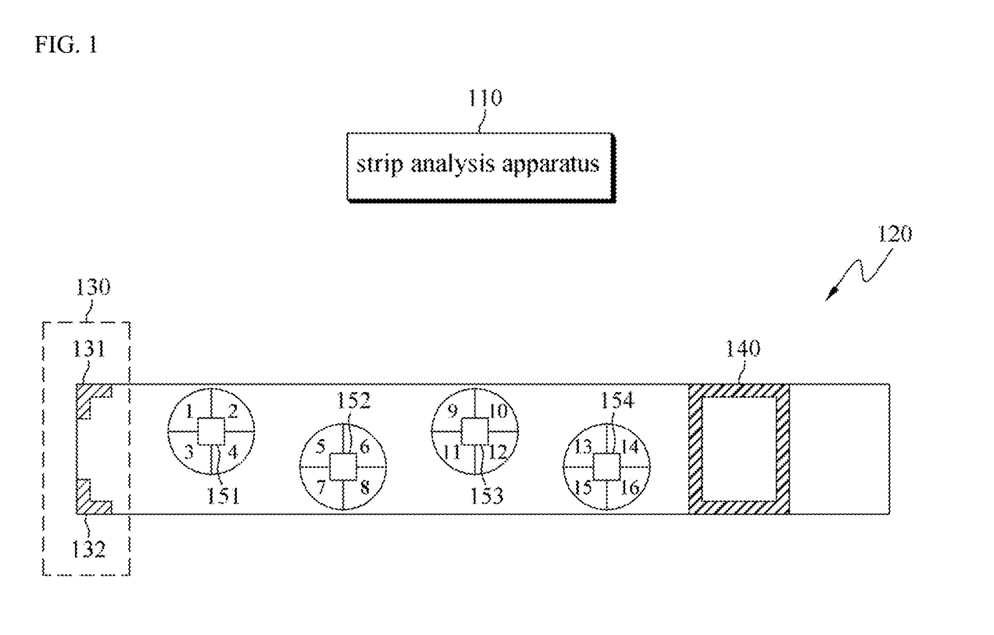
FIG. 1 is a diagram illustrating a urine test system according to an embodiment of the present disclosure.
Figure 2:
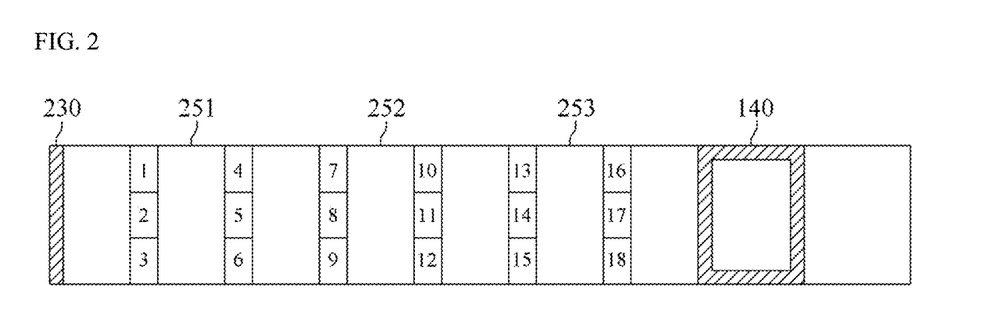
FIG. 2 is a diagram illustrating a urine test strip according to another embodiment of the present disclosure.

FIG. 1 is a diagram illustrating a urine test system according to an embodiment of the present disclosure, and FIG. 2 is a diagram illustrating a urine test strip according to another embodiment of the present disclosure.

Referring to FIG. 1, a urine test system according to an embodiment of the present disclosure may include a strip analysis apparatus 110 and a urine test strip 120.

The strip analysis apparatus 110 can include a camera capable of acquiring an image of the urine test strip 120, and in certain embodiments, the strip analysis apparatus 110 can receive input of a urine test strip image from an outside source instead of photographing the urine test strip directly. The strip analysis apparatus 110 can be, for example, a terminal such as a smart phone or tablet PC, etc., that includes a processor and a camera.

The strip analysis apparatus 110 may detect the reagent pads and colorimetric tables from the urine test strip image. As the urine test strip image can include background portions outside than the urine test strip 120, a preprocessing procedure of detecting the urine test strip within the urine test strip image may be needed.

The urine test strip 120 may include a first marker 130 and a second marker 140, with the reagent pads 151 to 154 and colorimetric tables arranged between the first and second markers 130, 140. The colorimetric tables may be arranged around the reagent pads 151 to 154, and FIG. 1 illustrates an example in which four colorimetric tables are arranged around the reagent pads. The areas denoted by the numerals 1 to 16 in FIG. 1 represent the colorimetric tables.

The colorimetric tables may display different colors and may be used for checking the degrees of color change in the adjacent reagent pads resulting from a reaction with the urine. As long as the reagent pads and colorimetric tables are arranged between the first and second markers, the numbers and forms of the reagent pads 251 to 253 and colorimetric tables 1 to 18 and the distances between reagent pads or between colorimetric tables can be varied, as illustrated in FIG. 2, which shows another embodiment of a urine test strip.

The strip analysis apparatus 110, by using a first and a second marker image, can detect the area that includes the reagent pads 151 to 154 and colorimetric tables and is arranged between the first and second markers 130, 140 within the urine test strip image. The first and second markers can be of various forms that can be detected in the image, and as illustrated in FIG. 2, the first marker 230 can have the form of a strip located at one end of the urine test strip.

The strip analysis apparatus 110 can detect the reagent pads and colorimetric tables of the urine test strip image by matching the areas of interest, which represent the positions of the reagent pads and colorimetric tables of the urine test strip, with the area between the first and second marker images. Further, the strip analysis apparatus 110 can compare the color of a detected reagent pad with the colors of a colorimetric table and determine the color of the reagent pad to be the color having the highest degree of similarity from among the colors of the colorimetric table. The strip analysis apparatus 110 can use the color of the reagent pad thus determined to output the urine test result.

The method of detecting the urine test strip performed by the strip analysis apparatus is described below in further detail.

Figure 3:
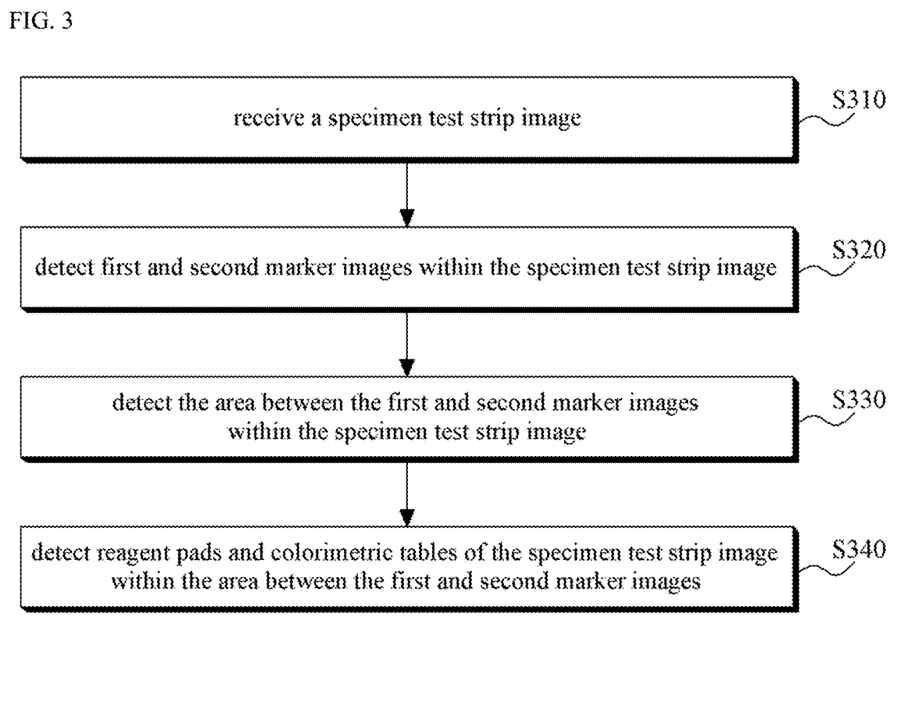
FIG. 3 is a flow diagram for a method of detecting a urine test strip according to an embodiment of the present disclosure.
Figure 4:
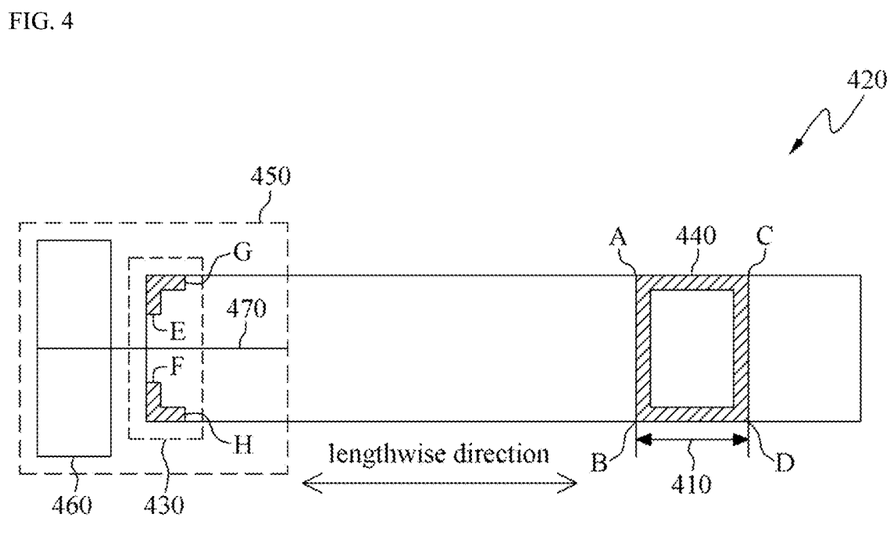
FIG. 4 is a diagram illustrating a method of detecting a first marker image according to an embodiment of the present disclosure.
Figure 5:
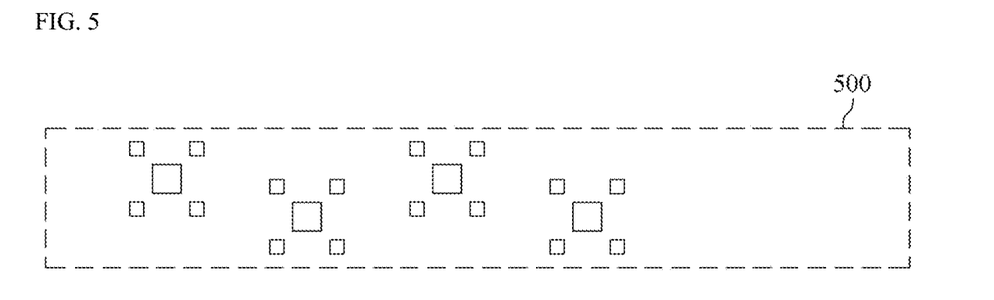
FIG. 5 is a diagram illustrating areas of interest according to an embodiment of the present disclosure.
Figure 6:
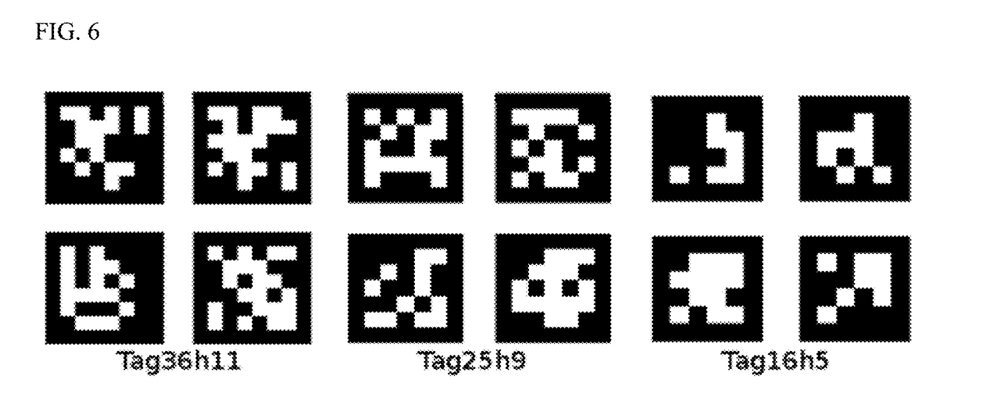
FIG. 6 is a diagram illustrating types of April tags.

FIG. 3 is a flow diagram for a method of detecting a urine test strip according to an embodiment of the present disclosure, and FIG. 4 is a diagram illustrating a method of detecting a first marker image according to an embodiment of the present disclosure. FIG. 5 is a diagram illustrating areas of interest according to an embodiment of the present disclosure, and FIG. 6 is a diagram illustrating types of April tags.

A strip analysis apparatus according to an embodiment of the present disclosure may receive, i.e. as input, a urine test strip image (S310), where the urine test strip image is a photographed image of a urine strip that includes a first and a second marker. The urine test strip image can be photographed by the strip analysis apparatus, or an image photographed with a separate camera can be provided to the strip analysis apparatus.

Then, the strip analysis apparatus may detect a first and a second marker image within the urine test strip image (S320). The markers can have shapes that allow easy recognition; for example, the April tags (Tag36h11, Tag25h9, Tag16h5) illustrated in FIG. 6 or QR codes can be utilized as markers. While certain embodiments can have the first and the second marker both implemented as April tags or QR codes, this can require an increased size of the urine test strip, and as such, April tags and QR codes can be used selectively. As illustrated in FIG. 1, the first marker 130 can include at least one marker located at the corner at one end of the urine test strip, where a pair 131, 132 of 'L'-shaped markers located at the corners on either side can be used. The second marker 140 can be an April tag or a QR code.

Unlike the case of the second marker, it can be difficult to recognize the first marker by shape, and therefore, the strip analysis apparatus may detect the first marker by using the relationship between the length of the urine test strip and the length of the second marker. A more detailed description is provided below, with reference to FIG. 1 and FIG. 4, of a method of detecting the first marker. Suppose FIG. 4 is a urine test strip image obtained by photographing the urine test strip 120 of FIG. 1, where FIG. 4 shows only the first and second marker images 430, 440 for the sake of convenience.

As illustrated in FIG. 1, there is a certain ratio between the length of the urine test strip 120 and the length of the second marker 140. For instance, if the ratio of the length of the second marker 140 to the length of the urine test strip 120 is 1:4, then in the urine test strip image also, the ratio of the length 410 of the second marker image to the length of the urine test strip 420 may also be 1:4. Also, as the first marker 130 is located at the distal end of the urine test strip 120, it can be easily estimated or ascertained that, in the urine test strip image, the first marker image 430 is located at a point that is four times as far from the position of the second marker image 440 as the length 410 of the second marker image 440. Here, the lengths of the second marker 140 and the second marker image 440 are lengths corresponding to the lengthwise direction of the urine test strip 120.

However, since the ratio of the length 410 of the second marker image 440 to the length of the urine test strip 420 may not be exactly 1:4 in the urine test strip image depending on the photography position, the strip analysis apparatus may determine a candidate area 450 separated apart from the second marker image 440 where the possibility of the first marker image 430 being located therein is high. Such candidate area 450 can be determined depending on the length 410 of the second marker image 440 and the ratio between the length of the urine test strip 120 and the length of the second marker 140.

When the candidate area 450 is determined, the strip analysis apparatus may move a window 460 of a preset size within the candidate area 450 and detect the first marker image 430 by using the pixel values within the window 460 and the color of the first marker 130.

For instance, the first marker 130 can be of a black color, and the strip analysis apparatus can detect the first marker image 430 based on the size of an area representing the minimum value of the pixel values within the window 460. The window 460 can be moved from the left side to the right along a center line 470 of the candidate area 450, and when the window 460 enters the area where the first marker image 430 is located, the area representing the minimum value of the pixel values would begin to increase. When the area representing the minimum value of the pixel values shows a maximum size and does not increase any further, the strip analysis apparatus can determine that the first marker image 430 is located in the corresponding area.

In other embodiments, the first marker 130 can be of a chromatic color or can include a pattern, and the strip analysis apparatus can detect the first marker image by using the pixel values within the window 460 in accordance with the color of the first marker 130.

Returning again to FIG. 3, the strip analysis apparatus may use the detected first and second marker images to detect an area between the first and second marker images within the urine test strip image (S330). Since the reagent pads and colorimetric tables of the urine test strip are located between the first and second markers as already described above, the strip analysis apparatus may detect the area between the first and second marker images where the reagent pads and colorimetric tables are included.

The strip analysis apparatus may detect the reagent pads and colorimetric tables in the urine test strip image in the area between the first and second marker images (S340). More specifically, the reagent pads and colorimetric tables of the urine test strip image may be detected (S340) by matching areas of interest, which represent the locations of the reagent pads and colorimetric tables of the urine test strip, with the area between the first and second marker images.

Referring to FIG. 5, the quadrilateral frames within the quadrilateral area 500 detected from the urine test strip image in FIG. 5 may be areas of interest, representing locations of the reagent pads and colorimetric tables of the urine test strip. These areas of interest can be generated based on the actual size of the urine test strip and the actual locations of the reagent pads and colorimetric tables, and referring to FIG. 1 and FIG. 5, it can be seen that the arrangement of the areas of interest may be similar to the arrangement of the actual reagent pads and colorimetric tables.

Therefore, when the quadrilateral area between the detected first and second marker images are matched with the areas of interest of FIG. 5, the reagent pads and colorimetric tables can be detected in the urine test strip image.

The areas of interest can be generated so as to be matched when the urine test strip is in a horizontal state, but the urine test strip image can be generated slanted from a perfectly horizontal line depending on the photography environment. Since the quadrilateral area between the first and second marker images may not overlap the areas of interest if the urine test strip image is slanted, the strip analysis apparatus can adjust the position of the area between the detected first and second marker images such that the areas of interest can overlap the area between the first and second marker images. For instance, the rotated angle of the first and second marker images can be calculated by way of image processing, to adjust the area between the first and second marker images to be horizontal.

In one example, the strip analysis apparatus can use a homography warping algorithm to convert the coordinates of the pixels within the area between the first and second marker images, thereby adjusting the position of the area between the first and second marker images.

Also, in cases where the urine test strip is photographed from very far away, the size of the urine test strip image can become smaller than the actual size of the urine test strip, resulting in the quadrilateral area between the first and second marker images not overlapping the areas of interest. Conversely, in cases where the urine test strip is photographed with magnification, the quadrilateral area between the first and second marker images may not overlap the areas of interest, either.

As such, depending on the size of the quadrilateral area between the first and second markers of the urine test strip, the strip analysis apparatus can adjust the size of the quadrilateral area between the first and second marker images detected in step S330, to match the quadrilateral area between the first and second marker images with the areas of interest.

Thus, according to an embodiment of the present disclosure, it is possible to accurately detect the areas where the reagent pads and colorimetric tables are located in a urine test strip image by using the actual sizes of the markers and the urine test strip.

Although the descriptions above refer to an example in which the ratio of the length of the second marker 140 to the length of the urine test strip 120 is 1:4, the relationship between the length of the second marker 140 and the length of the urine test strip 120 can have a ratio of 1:10 or any of a variety of ratios according to different embodiments.

Also, according to another embodiment of the present disclosure, the first marker 130 of the urine test strip 120 can also be an April tag or a QR code. It is possible for a urine test strip 120 to be bent by the weight of the urine disposed on the distal end or for the image of the strip to be distorted depending on the angle between the strip and the camera, whereby the first marker image may also be bent within the urine test strip image, and a strip analysis apparatus according to an embodiment of the present disclosure can calculate the degree of distortion, such as the angle in which the first marker image is bent, etc., from pre-stored information regarding the size and shape of the first marker. Then, according to the calculation results, the quadrilateral area can be corrected such that the quadrilateral area between the first and second marker images overlaps the areas of interest.

Also, various primary colors can be arranged between the first and second markers 130, 140 of the urine test strip 120 for correcting the effects of shadows or lighting. For instance, primary colors such as red, yellow, green, blue, black, etc., can be arranged printed on the urine test strip 120, where such primary stamps can be arranged on both sides of the colorimetric tables, i.e. on the edges of the urine test strip 120 along the lengthwise direction of the urine test strip 120.

Figure 7:
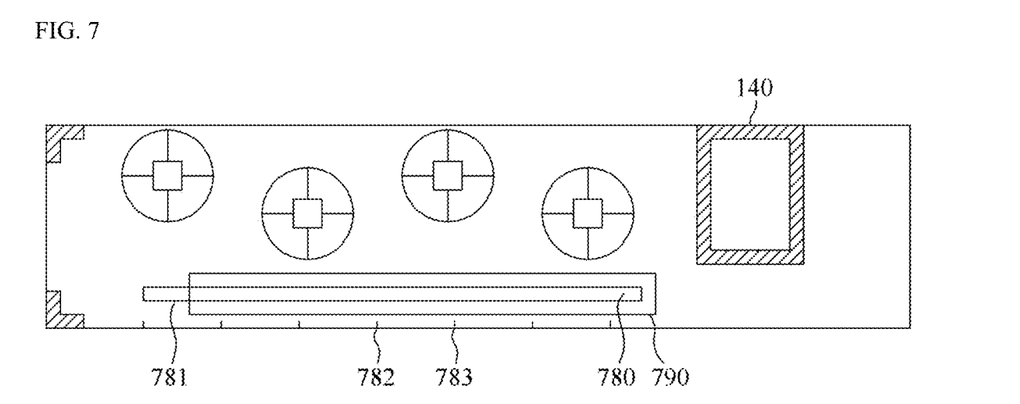
FIG. 7 and FIG. 8 are diagrams illustrating urine test strips according to other embodiments of the present disclosure.
Figure 8:
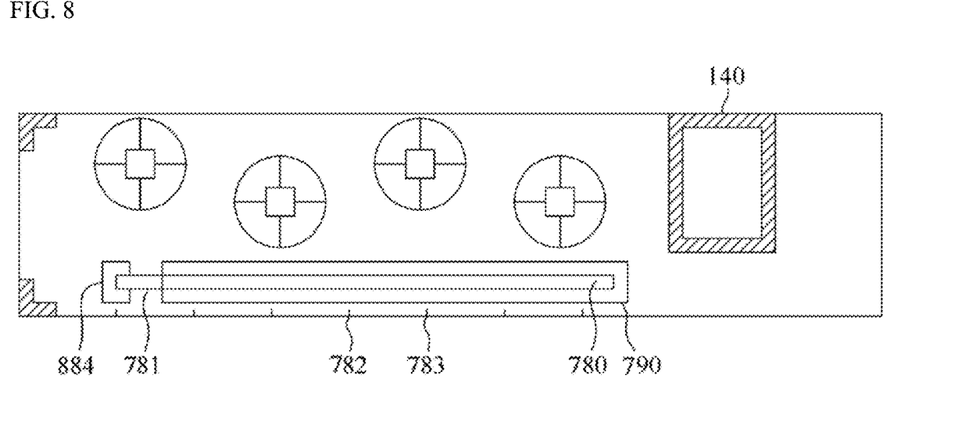
Figure 9:
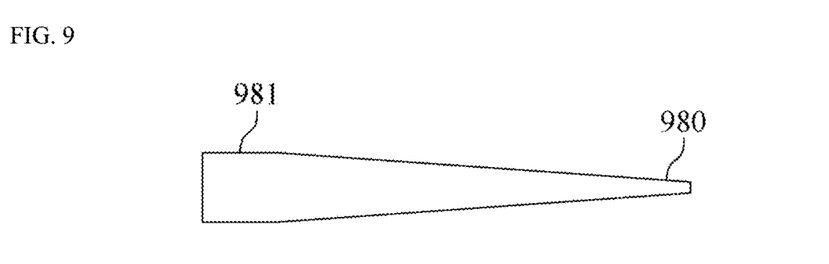
FIG. 9 is a diagram illustrating a timer according to another embodiment of the present disclosure.

FIG. 7 and FIG. 8 are diagrams illustrating urine test strips according to other embodiments of the present disclosure, and FIG. 9 is a diagram illustrating a timer according to another embodiment of the present disclosure.

A urine test strip according to an embodiment of the present disclosure may include a multiple number of reagent pads, colorimetric tables, a timer, and a waterproof film. The colorimetric tables can be arranged in the surrounding area of the respective reagent pads.

The urine test strip illustrated in FIG. 7, as compared to the urine test strip of FIG. 1, may further include a timer 780 and a waterproof film 790. The timer 780 may indicate the urine immersion time and may include an immersion area 781 that is to be immersed in urine.

Since the colors of the reagent pads may continue to change after urine is disposed, the accuracy of color analysis can be increased by acquiring the urine test strip image and analyzing the color of the reagent pads after a certain duration of time has passed since urine immersion, rather than photographing the urine test strip and analyzing the color of the reagent pads immediately after the urine test strip is immersed in urine. Thus, an aspect of the present disclosure proposes the technological spirit of including a timer on the urine test strip.

The timer 780 can be provided with a material such as paper, nonwoven fabric, etc., that is capable of drawing in the absorbed moisture by way of capillary action. For example, in cases where paper is used for the timer, the urine absorbed in the immersion area 781 may be absorbed by capillary action in the direction of the end of the timer 780 located at the opposite side of the immersion area 781, thus being gradually moved according to the passage of time. In the case of a colored paper, the portion wetted by the moisture and the portion not yet wetted may exhibit a visually discernible difference, and thus the section of the timer 780 that has undergone a color change due to urine immersion may increase with the passage of time.

Consequently, the length of the section that undergoes a color change in the timer 780 may correspond to the duration of time that has passed since the urine immersion, and the urine immersion time can be estimated from the length of the section that has changed color in the timer 780.

A urine test strip according to an embodiment of the present disclosure can further include markings for enabling the user to readily check the length of the section that has changed color, and such markings may be located in the vicinity of the timer 780.

If the urine test strip has been configured such that the optimal color analysis time range for determining the color of the reagent pads is when the end of the section of color change is between the fourth marking 782 and fifth marking 783, then the user can determine that the optimal testing time point has arrived when the end of the section of color change in the timer on a urine test strip being used in a test is between the fourth marking 782 and fifth marking 783 and can thus photograph the urine test strip used in the test by way of the strip analysis apparatus.

According to another embodiment of the present disclosure, a urine supply part 884 can further be included, as illustrated in FIG. 8, to retain the urine and supply the urine to the immersion area 781. The urine supply part 884 can retain a sufficient amount of urine such that a sufficient amount of urine may be provided to the timer from the immersion area 781. The urine supply part 884 can be arranged at a position corresponding to the immersion area 781 and, in one example, can be a thick pad for absorbing urine or a hole for storing urine.

If the timer 780 has a constant or uniform width, as illustrated in FIG. 7, then the speed by which the length of the section that has undergone a color change would decelerate with the passage of time. Thus, it may be preferable to set the optimal color analysis time range in consideration of this phenomenon. Alternatively, in order that the speed by which the length of the section of color change increases due to capillary action may remain constant, the timer 980 can be formed such that the width decreases along the direction of increasing distance from the immersion area 981, as illustrated in FIG. 9.

Using the timer 780 to estimate the accurate urine immersion time requires that the area of the timer 780 other than the immersion area 781 of the timer 780 be prevented from being immersed in the urine. Thus, a urine test strip according to an embodiment of the present disclosure can further include a waterproof film 790 that prevents urine immersion for the remaining area of the timer 780 other than the immersion area 781. That is, the waterproof film 790 may leave only a portion of the timer 780 open as the immersion area 781.

The waterproof film 790 can be formed to overlap the entirety of the remaining area of the timer 780 other than the immersion area 781 or, depending on the length of the timer 780, overlap a portion of the remaining area of the timer 780 excluding the immersion area 781.

As the user must be able to visually inspect the color change section of the timer, it may be preferable that the waterproof film overlapping the timer be of a transparent material.

Thus, according to an embodiment of the present disclosure, a timer can be used to ascertain the accurate analysis time for the urine test strip.

Figure 10:
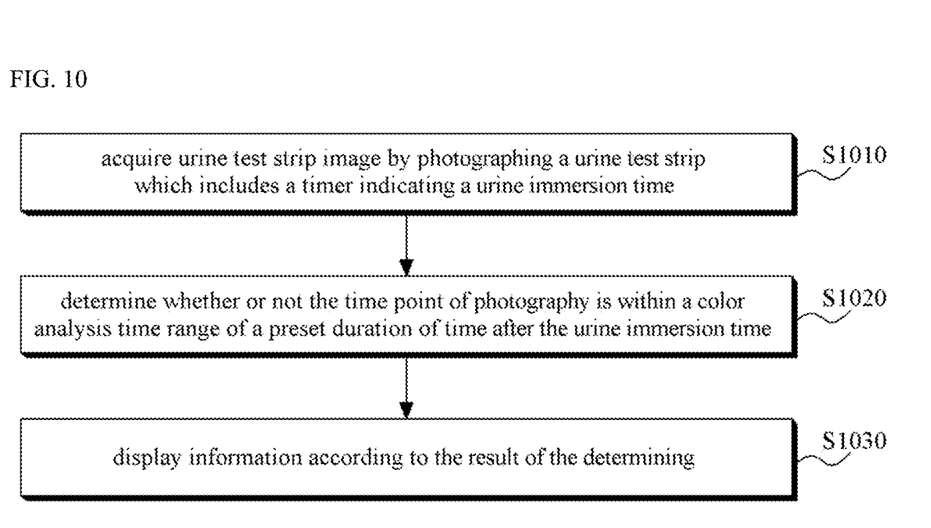
FIG. 10 is a flow diagram for a method of analyzing a urine test strip according to an embodiment of the present disclosure.

FIG. 10 is a flow diagram for a method of analyzing a urine test strip according to an embodiment of the present disclosure.

A strip analysis apparatus according to an embodiment of the present disclosure may photograph a urine test strip, which includes a timer for indicating the urine immersion time, to acquire a urine test strip image (S1010). Here, the timer can be a timer in which the section that changes color due to urine immersion increases according to the passage of time.

Further, the strip analysis apparatus may analyze the timer image included in the urine test strip image to determine whether or not the time point of photography lies within a color analysis time range, which may be defined by a preset duration of time after the urine immersion time (S1020). As described above with reference to FIG. 7, if the color analysis time range has been configured to be between the fourth marking and fifth marking of the urine test strip, then the strip analysis apparatus can determine whether or not the time point of photography lies within the color analysis time range by analyzing whether or not the end of the color change section of the timer at the time point of photography is positioned between the fourth and fifth markings.

Then, the strip analysis apparatus may display information according to the result of the determining (S1030). The strip analysis apparatus can be equipped with a display device for the displaying of information and may display different information depending on whether it is determined that the time point of photography is included or is not included within the color analysis time range.

If the time point of photography is included in the color analysis time range, the strip analysis apparatus may display the results of the urine test. The strip analysis apparatus can analyze the colors of the reagent pads by using the method of detecting the urine test strip described above and subsequently display the urine test results.

Cases in which the time point of photography is outside the color analysis time range may include two types. One is when the time point of photography has not yet reached the color analysis time range, and the other is when the time point of photography has passed beyond the color analysis time range. If the time point of photography has not yet reached the color analysis time range, then the strip analysis apparatus may display reshoot time information. For instance, where the color analysis time range is set to be between the fourth marking and fifth marking of the urine test strip, if the time point of photography corresponds to a point between the third marking and fourth marking of the urine test strip, then the strip analysis apparatus can calculate the remaining time until the color analysis time range and display the reshoot time information. The strip analysis apparatus can also calculate the remaining time based on the speed by which the length of the section undergoing a color change increases.

If the time point of photography has passed beyond the color analysis time range, then the strip analysis apparatus can display reshoot request information, requesting the user to immerse a new urine test strip in urine and reshoot the image.

The technology described above can be implemented in the form of program instructions that may be performed using various computer means and can be recorded in a computer-readable medium. Such a computer-readable medium can include program instructions, data files, data structures, etc., alone or in combination. The program instructions recorded on the medium can be designed and configured specifically for the embodiments or can be a type of medium known to and used by the skilled person in the field of computer software. A computer-readable medium may include a hardware device that is specially configured to store and execute program instructions. Some examples may include magnetic media such as hard disks, floppy disks, and magnetic tapes, optical media such as CD-ROM's and DVD's, magneto-optical media such as floptical disks, and hardware devices such as ROM, RAM, flash memory, etc. Examples of the program of instructions may include not only machine language codes produced by a compiler but also high-level language codes that can be executed by a computer through the use of an interpreter, etc. The hardware mentioned above can be made to operate as one or more software modules that perform the actions of the embodiments, and vice versa.

While the present disclosure is described above by way of limited embodiments and drawings that refer to particular details such as specific elements, etc., these are provided only to aid the general understanding of the present disclosure. The present disclosure is not to be limited by the embodiments above, and the person having ordinary skill in the field of art to which the present disclosure pertains would be able to derive numerous modifications and variations from the descriptions and drawings above. Therefore, it should be appreciated that the spirit of the present disclosure is not limited to the embodiments described above. Rather, the concepts set forth in the appended scope of claims as well as their equivalents and variations are encompassed within the spirit of the present disclosure.

What is claimed is:

1. A method of detecting a urine test strip, the method comprising:
   receiving input of a urine test strip image, the urine test strip image being a photographed image of a urine test strip including a first marker and a second marker;
   detecting a first marker image and a second marker image within the urine test strip image;
   detecting an area between the first and second marker images within the urine test strip image; and detecting a reagent pad and a colorimetric table in the urine test strip image by matching an area of interest with the area between the first and second marker images, the area of interest representing a position of the reagent pad and the colorimetric table in the urine test strip image, wherein the detecting of the first and second marker images comprises:

determining a candidate area for the first marker image within the urine test strip image by using a relationship between a length of the urine test strip and a length of the second marker; and detecting the first marker image by using a pixel value within a window of a preset size and a color of the first marker while moving the window within the candidate area, wherein the first marker comprises at least one marker positioned at a corner on one end of the urine test strip, and wherein the reagent pad and the colorimetric table of the urine test strip are positioned between the first marker and the second marker.

2. The method of detecting a urine test strip according to claim 1, wherein the second marker comprises an April tag or a QR code.

3. The method of detecting a urine test strip according to claim 1, wherein the first marker of the urine test strip has a chromatic color or includes a pattern, and the detecting of the first marker image comprises:

detecting the first marker image by using the pixel values within the window in accordance with the color of the first marker while moving the window along a center line of the candidate area.

4. The method of detecting a urine test strip according to claim 1, wherein the determining of the candidate area for the first marker image comprises:

determining the candidate area separated from the second marker image, a separated distance between the second marker image and the candidate area is determined based on a length of the second marker image and a ratio between a length of the urine test strip and a length of the second marker, and the lengths of the second marker and the second marker image are lengths corresponding to a lengthwise direction of the urine test strip.

5. The method of detecting a urine test strip according to claim 1, wherein the first marker of the urine test strip has a black color, and the detecting of the first marker image comprises:

detecting the first marker image based on a size of an area exhibiting a minimum value from among pixel values within the window.

6. The method of detecting a urine test strip according to claim 1, wherein the detecting of the reagent pad and the colorimetric table in the urine test strip image comprises:

correcting the area between the first and second marker images based on a degree of distortion of the first marker image such that the area of interest overlaps the area between the first and second marker images.

7. The method of detecting a urine test strip according to claim 1, wherein the detecting of the area between the first and second marker images comprises:

detecting the area between the first and second marker images as determined by two of vertices of the second marker image and a distal end of the first marker image.

8. The method of detecting a urine test strip according to claim 1, wherein the detecting of the reagent pad and the colorimetric table in the urine test strip image comprises:

adjusting a position of the area between the first and second marker images such that the area of interest overlaps the area between the first and second marker images.

* * * * *